United States Patent [19]

Arii et al.

[11] 3,943,755

[45] Mar. 16, 1976

[54] METHOD AND APPARATUS FOR MEASURING THE MAGNITUDE OF A CLAMPING LOAD APPLIED TO A LAMINATED IRON CORE OF AN ELECTRIC MACHINE

[75] Inventors: Mitsuru Arii, Tokyo; Hideo Kashiwaya, Yokohama; Kuniharu Uchida, Tokyo, all of Japan

[73] Assignee: Tokyo Shibaura Electric Co., Ltd., Kawasaki, Japan

[22] Filed: Oct. 22, 1974

[21] Appl. No.: 517,026

[52] U.S. Cl. ................................ 73/67.5 R
[51] Int. Cl.[2] .................................. G01N 9/24
[58] Field of Search ................... 73/67.5 R, 67.6

[56] References Cited
UNITED STATES PATENTS

| | | | |
|---|---|---|---|
| 2,612,772 | 10/1952 | McConnell | 73/67.5 R |
| 3,066,525 | 12/1962 | Harris | 73/67.5 R |
| 3,101,608 | 8/1963 | Benson et al. | 73/67.5 R |
| 3,453,872 | 7/1969 | Botsco | 73/69 |

OTHER PUBLICATIONS

Hughes et al., The Evaluation of Bond Quality in Honeycomb Panels using Ultrasonic Surface Wave Techniques, Nondestructive — Testing, Vol. 17, No. 6, Nov.–Dec., 1959, pp. 373–377.

*Primary Examiner*—James J. Gill
*Assistant Examiner*—Anthony V. Ciarlante
*Attorney, Agent, or Firm*—Oblon, Fisher, Spivak, McClelland & Maier

[57] ABSTRACT

Method and apparatus for measuring the magnitude of a clamping load applied to a laminated iron core of an electric machine which comprises the steps of introducing a sound wave into a laminated iron core of an electric machine at one end face thereof and immediately generating a first electric signal; producing a second electric signal when the sound wave passes through the core body and reaches the opposite end face thereof; measuring a time interval between the emission of the first electric signal and that of the second electric signal; dividing a distance between both end faces of the laminated iron core by the measured time interval to calculate the velocity of a sound wave vertically propagating through the laminated iron core; and determining the measured magnitude of clamping load applied to said core from the calculated propagating velocity of a sound wave with reference to previously prepared data on a relationship between the magnitude of clamping load applied to the core and the corresponding propagating velocity of a sound wave.

10 Claims, 8 Drawing Figures

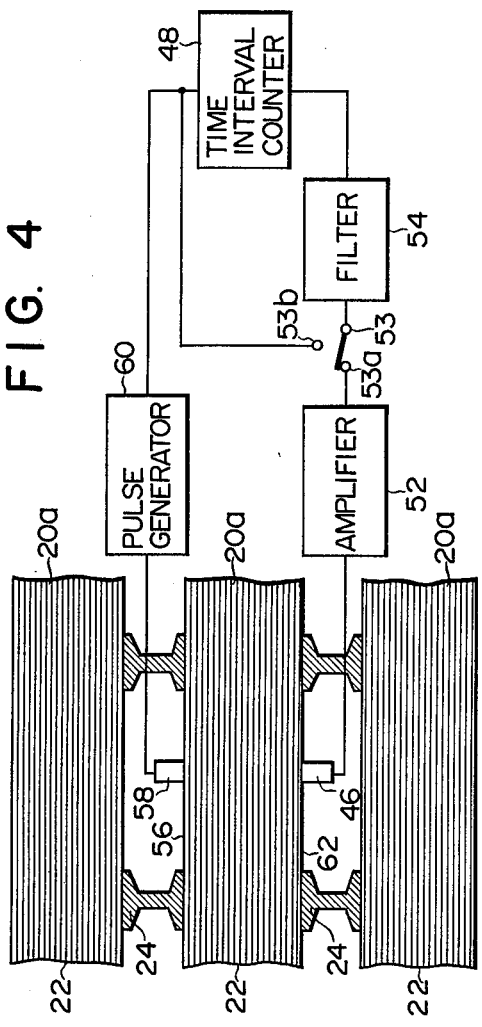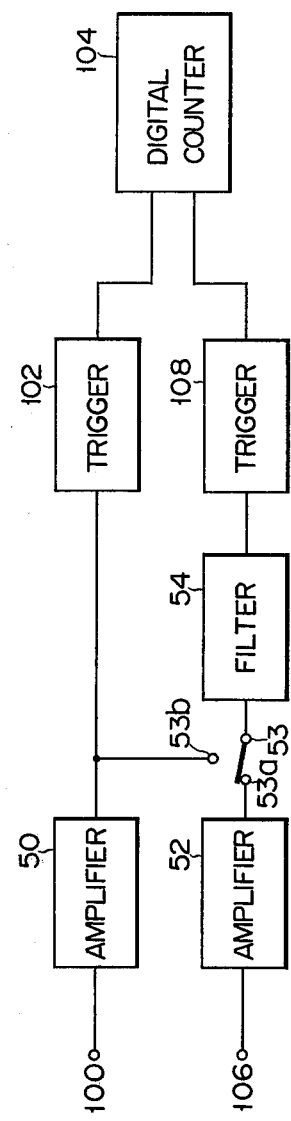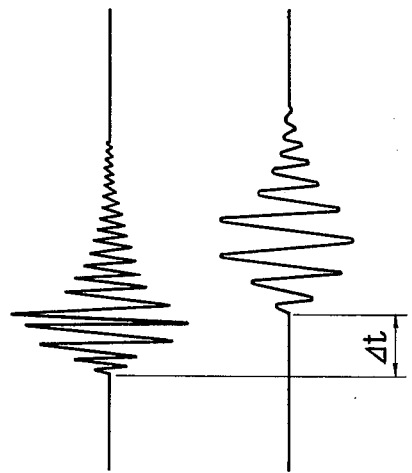

METHOD AND APPARATUS FOR MEASURING THE MAGNITUDE OF A CLAMPING LOAD APPLIED TO A LAMINATED IRON CORE OF AN ELECTRIC MACHINE

BACKGROUND OF THE INVENTION

This invention relates to a method and apparatus for measuring the magnitude of a clamping load applied to a laminated iron core used with an electric machine by calculating the velocity of a sound wave propagating through the laminated iron core in the direction of lamination.

The magnitude of clamping pressure initially applied to the tightened surface of a laminated iron core used with an electric machine gradually decreases due to time-worn conditions such as the driness of insulation varnish baked to both sides of the respective member plates of the core. In extreme cases, the constituent member plates of a laminated iron core are loosened, resulting in the vibration of the core plates, or what is worse, in the occurrence of accidents. As used herein, the term "clamping pressure on the tightened surface" is defined to mean a quotient arrived at by dividing the magnitude of clamping load applied to a laminated iron core by the area of the tightened end face of said core.

Hitherto, the magnitude of clamping load applied to a laminated iron core, therefore, the clamping pressure has been determined by measuring a strain sustained by clamping bolts. The customary pressure measuring process consists in fitting a strain gauge to each of the clamping bolts to measure strains sustained by said bolts themselves due to their action to clamp a laminated iron core; converting measured strains into stresses imparted to said bolts; multiplying the stresses by the total cross sectional areas of the clamping bolts to calculate clamping load imparted to said bolts; and finally determining the magnitude of clamping pressure applied to the tightened end face of a laminated iron core from the product of said multiplication.

However, the conventional pressure measuring process using a strain gauge has the drawbacks that it can not find the magnitude of clamping load applied to the local points on the end face of a laminated iron core, though it may determine the magnitude of average clamping load applied to the entire end face of the core; and the strain gauge is subject to the gradually decreased precision of measurement due to its time-worn deterioration, failing to trace time change in the magnitude of clamping load or clamping load applied to a laminated iron core used with an electric machine over a long period with a constant degree of precision.

SUMMARY OF THE INVENTION

It is accordingly the object of this invention to provide a method and apparatus for measuring the magnitude of a clamping load applied to a laminated iron core of an electric machines which are free from the drawbacks accompanying the prior art clamping load-measuring method and apparatus, and can measure the various magnitudes of pressure applied to local points on the end face of the laminated iron core and in consequence the distribution of said magnitudes and carry out said measurement with high precision over a long period.

To attain the above-mentioned object, this invention utilizes the fact that the velocity of a sound wave propagating through a laminated iron core in the direction of lamination varies with the magnitude of clamping load applied to the core. Namely, the pressure-measuring apparatus of the invention comprises a device for introducing a sound wave into the laminated iron core at one end face thereof; a device for generating a first electric signal when a sound wave is brought into the core; a device for giving forth a second electric signal when the sound wave propagates through the core body and reaches the opposite end face of the core; and a device for measuring a time interval between the emissions of the first and second electric signals, thereby measuring the magnitude of clamping load applied to the laminated iron core from said time interval. To describe in detail, the clamping load-measuring method of this invention consists in calculating the propagating velocity of a sound wave from a quotient arrived at by dividing a distance between both end faces of a laminated iron core by the above-mentioned time interval and finally determining the magnitude of clamping load applied to the core from the calculated propagating velocity of a sound wave with reference to previously prepared data on a relationship between the clamping load and the corresponding propagating velocity of a sound wave.

A sound wave can be introduced into a laminated iron core at one end face thereof simply by knocking said end face with a wodden mallet.

In this case, that end face of the core is fitted with a first electric signal-generating device. Another process of introducing a sound wave into the laminated iron core consists in providing a pulse generator and a sound wave generator actuated by an output from said pulse generator attached to one end face of the core. In this case, an output from the pulse generator constitutes a first electric signal.

The distribution of various magnitudes of clamping load applied to a laminated iron core can be determined by fitting a first electric signal-generating device or sound wave generator to several points on one end face of the core and a second electric signal-generating device similarly to various points on the opposite end face of the core.

Further, a stable distinct measurement of clamping load applied to a laminated iron core can be effected by providing, is necessary, an amplifier to supply a time interval-measuring device with first and second electric signals at a proper level and fitting a second electric signal-transmitting circuit with a filter allowing the passage of only a sound wave of relatively low frequency which has propagated through a laminated iron core at a slow rate, but obstructing the passage of a sound wave of relatively high frequency which has quickly propagated through the rigid portion of the core such as the clamping bolts.

The time interval-measuring device may consist of a known type, such as an electromagnetic oscillograph, Braun tube oscillograph or digital counter. It is also possible to supply a measured time interval to a computer, calculate the propagating velocity of a sound wave according to a program previously stored in a memory device to determine the magnitude of clamping load applied to a laminated iron core and, if desired, print out a required value of tightening pressure by connecting a printer to the computer.

As mentioned above, this invention attains easy measurement of various magnitudes of clamping load applied to local points of a laminated iron core and in consequence the distribution of said magnitudes by fitting first electric signal-generating device, second electric signal-generating device and sound wave generator to the core at any time and location of measurement without the necessity of applying any additional mechanical work to the core or associated members thereof or removing said associated members from the core. Further, the apparatus of this invention effects the measurement of clamping load applied to a laminated iron core with high precision over a long period and in consequence the tracing of time change in the magnitude of said clamping load. It is therefore possible by utilizing the abovementioned advantages to apply a uniform degree of clamping load to every part of a laminated iron core when it is incorporated in an electric machine, and trace time change in the magnitude of said clamping load after the electric machine has been delivered from a manufacturing plant and, where necessary, carry out the additional clamping of the core. Thus the clamping load measuring apparatus of this invention is applicable over a very wide field.

BRIEF DESCRIPTION OF THE DRAWING

FIG. 3 presents the oscillograms of the first and second electric signals, showing a time interval therebetween;

FIG. 4 is a fractional cross sectional view of another embodiment of the invention for measuring the magnitude of clamping load applied to a local point on one end face of a laminated iron core;

FIG. 5 is a block circuit diagram of still another embodiment of the invention where the time interval-measuring device consists of a digital counter;

DESCRIPTION OF THE PREFERRED EMBODIMENTS

Figure 1:
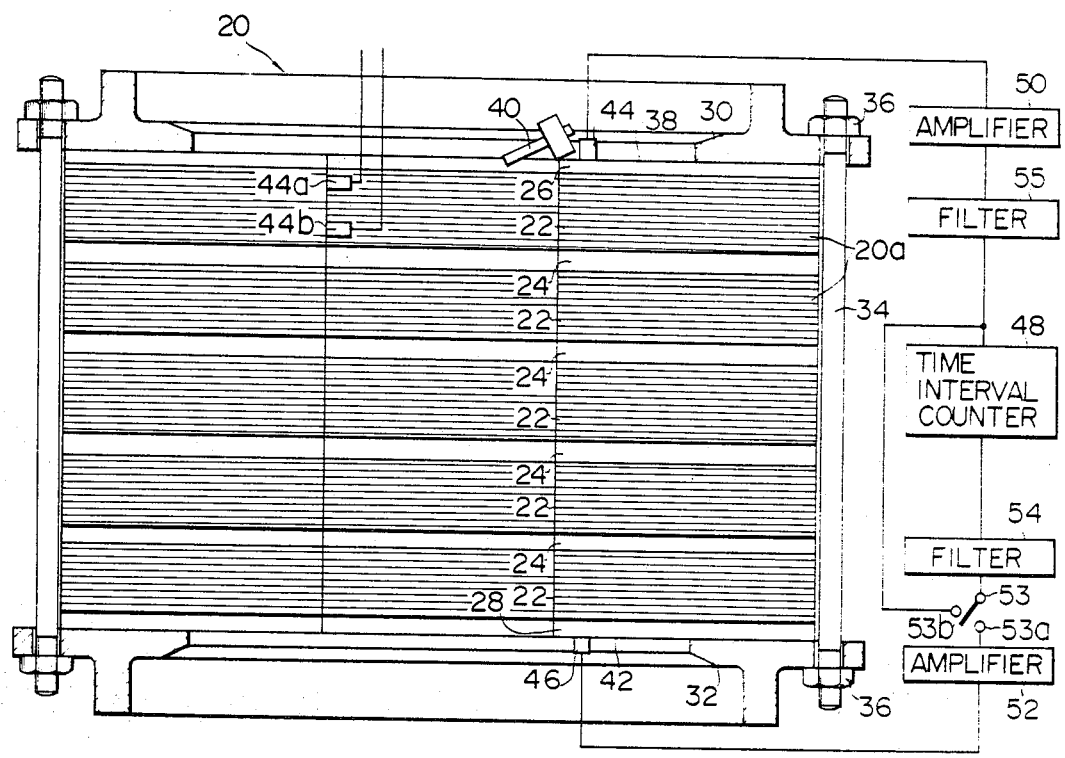
FIG. 1 is a fractional cross sectional view of an embodiment of this invention for measuring the magnitude of clamping load applied to the stator of an electric machine, for example, a generator or motor.

Referring to FIG. 1, numeral 20 shows a laminated iron core used as the stator of an electric machine, for example, a generator or a motor. The laminated iron core 20 comprises several core members 20a each formed of numerous iron sheets laminated to a prescribed thickness, internal spacers 24 interposed between the respective core members 20a and external spacers 26, 28 disposed between both end faces of the core 20 and the upper and lower flanges 30, 32 mounted on said end faces. The core 20 is firmly tightened from above and below by means of the upper and lower flanges 30, 32, clamping bolts 34 and nuts 36. One end face 38 of the core 20 is fitted with a first electric signal-generating device and the opposite end face 42 thereof with a second electric signal-generating device 46.

When one end face 38 of the lamined iron core 20 is struck with a wooden mallet 40, the resultant sound wave actuates the first electric signal-generating device to produce a first electric signal S1. Part of said sound wave quickly propagates through the rigid portions of the core such as flanges 30, 32, clamping bolts 34 and nuts 36 screwed to both ends of each clamping bolt 34 and actuates the second electric signal-generating device 46 to generate an output signal S2-$a$. The remainder of the above-mentioned sound wave is slowly transmitted through the core 20 itself with a certain time delay and similarly actuates the second electric signal-generating device 46 to produce another output signal S2-$b$. For the object of this invention, however, the latter output signal S2-$b$ from the second electric signal-generating device 46 is referred to as "the second electric signal".

The first electric signal-generating device 44 and second electric signal-generating device 46 permissibly consist of various types, for example, a piezoelectric element or magnetostrictive element. One type is a P.M. accelerometer manufactured by Bruel & Kjaer Company of Denmark. This accelerometer is formed of a piezoelectric element such as a crystal vibrator and, when subjected to vibrations, generates an electric signal across both electrodes surrounding the piezoelectric element. When electric pulses are impressed across both electrodes of the piezoelectric element of the above-mentioned type of sound wave detector, then said piezoelectric element commences vibrations at its natural frequency to introduce a sound wave into the laminated iron core at one end face thereof. Both electric signal-generating devices 44, 46 may be bonded to the end face of the laminated iron core 20 by adhesive or fitted thereto magnetically, as described in a pamphlet on the above-mentioned accelerometer of Bruel & Kjaer Company.

As shown in FIG. 1, a first electric signal emitted by the generator 44 is supplied to a time interval-measuring device 48 through an amplifier 50 and filter 55. Since, however, the first electric signal is normally strong, the amplifier 50 can be omitted. Though usually not required, the filter 55 may advisably be used, where external noises are expected to contaminate the first electric signal, leading to the inaccurate measurement of clamping load applied to a laminated iron core. A second electric signal S2-6 given forth by the generator 46 is conducted to the time interval-measuring device 48 through the amplifier 52 and filter 54. The reason is that since a sound wave actuating the second electric signal-generating device 46 is attenuated during propagation, the resultant weak second electric signal S2-$b$ has to be amplified to a proper level by the amplifier 52 before delivered to the time interval-measuring device 48 and that the filter 54 generally consisting of a band pass filter eliminates the high frequency signal component S2-$a$ quickly passing through the rigid portion of the core 20 such as the clamping bolts 34, nuts 36 and flanges 30, 32 and only allows the second electric signal S2-$b$ denoting a sound wave slowly traveling through the core 20 to be transmitted to the time interval-measuring device 48 and further prevents any external noise signal from being carried into said time interval-measuring device 48. Experiments show that the second electric signal S2-*b* showing a sound wave propagating through the laminated iron core 20 had a frequency of 1 to 2 kHz. If necessary, either or both of the first electric signal S1 and second electric signal S2-*b* are amplified distinctly to determine a time interval between these two electric signals when they reach the time interval-measuring device 48. Since, however, an electric signal passing through the filter 54 has its transmission slightly delayed, said delay is determined to correct a time interval between the first and second electric signals S1, S2-*b* measured by the time interval-measuring device 48. Though two filters 54, 55 are used in the first embodiment of FIG. 1, the figure only shows for simplification of illustration a circuit for measuring the time delay of an electric signal conducted through the filter 54. When a switch 53 touches a contact 53*a*, an ordinary time interval between the first and second electric signals S1, S2-*b* is determined. When, however, the operation of the switch 53 is changed over to touch a contact 53*b*, then the time interval-measuring device 48 measures a time interval between the first electric signal S1 directly delivered to said device 48 only through the amplifier 50, filter 55 and delayed first electric signal S1 conducted to said device 48 through the amplifier 50 and filter 55, as well as purposely through the filter 54, namely, the time delay sustained by said first electric signal S1 during transmission through the filter 54. The time delay of an electric signal conducted through the filter 55 can be measured to the same manner by the corresponding time delay-measuring circuit (not shown). Measurement of the time delay of the first electric signal S1 purposely conducted through the filter 54 provided a correct time interval between the first and second electric signals S1, S2-*b* when they reach the time interval-measuring device 48. Thus the actual velocity of a sound wave slowly propagating through the core 20 is calculated from the corrected time interval between the first and second electric signals S1, S2-*b*, thereby determining the magnitude of clamping load applied to the laminated iron core 20 through which a sound wave slowly propagates, with reference to previously prepared data on a relationship between the clamping load and the corresponding propagating velocity of a sound wave.

The time interval-measuring device 48 may consist of any of various types such as an electromagnetic oscillograph, Braun tube oscillograph and digital counter. Further, as previously mentioned, it is possible to supply an output from the digital counter to a computer, correct a measured time interval between the first and second electric signals S1, S2-*b* by measuring the time delay of the first electric signal S1 purposely caused to travel through the filter 54 so as to calculate the actual velocity of a sound wave propagating through a laminated iron core 20, determine the magnitude of clamping load applied to the core 20 which corresponds to said propagating velocity of a sound wave, all in accordance with a program previously stored in a memory device, and, if desired, record a required value of tightening pressure on a printer connected to the computer. All the electric and mechanical devices required for the above-mentioned operation may consist of the known types.

Referring to FIG. 1, the first electric signal-generating device 44 is fitted to one end face 38 of the laminated iron core 20 and the second electric signal-generating device 46 to the opposite end face 42 of said core 20. Where both electric signal-generating devices 44, 46 are placed at different points on the end faces 38, 42, respectively, the distribution of the magnitudes of clamping load applied to the laminated iron core 20 can be determined. Where the laminated iron core 20 constitutes the stator of a motor or generator as shown in FIG. 1 magnitudes of clamping load applied to various points in a horizontal plane ranging from the yoke member to the proximity of the slots of the core 20 can be determined to find the horizontal distribution of said magnitudes. Further where, as shown in FIG. 1, first and second electric signal-generating devices 44*a*, 44*b* are successively fitted to part of the peripheral side wall of the respective core members 20*a* consisting of laminated iron sheets to determine the magnitudes of clamping load applied to said core members 20*a*, then the distribution of said magnitudes in a vertical or laminated direction of the core 20 can be found.

Figure 2:
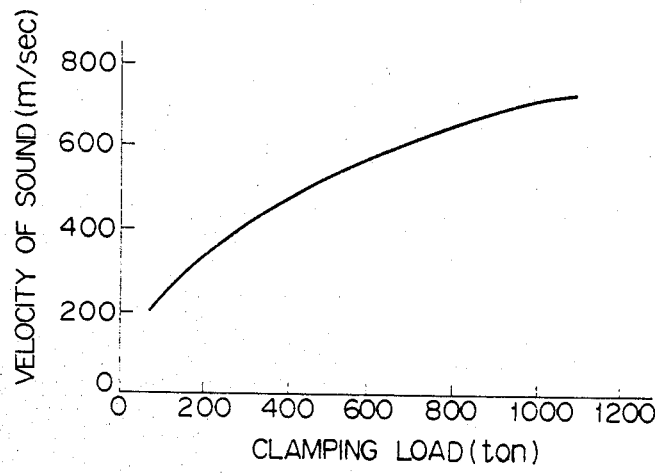
FIG. 2 is a graph showing a relationship between the magnitude of clamping load applied to a laminated iron core and the corresponding velocity of a sound wave propagating through the core.

FIG. 2 presents experimental data on a relationship between the magnitude of clamping load applied to a laminated iron core 20 and the corresponding velocity of a sound wave propagating through said core 20. In FIG. 3, the upper oscillogram obtained on an electromagnetic oscillograph used as the time interval-measuring device 48 represents the first electric signal S1 and the lower oscillogram shows the second electric signal S2-*b*. The notation $\Delta t$ of FIG. 3 shows a measured time interval between the first and second electric signals S1, S2-*b*. Since, however, the time required for the second signal S2-*b* to reach the time interval-measuring device 48 includes the time delay sustained by said second signal S2-*b* during transmission through the filter S4, said time interval $\Delta t$ has to be later corrected by the extent of the time delay.

The embodiment of FIG. 4 shows the case where measurement is made of the magnitude of clamping load applied to part of the respective core members 20*a* consisting of laminated iron sheets 22 and separated by intervening spacers 24. In this embodiment, a sound wave is introduced by a different process from FIG. 1. Namely, one end face 56 of each core member 20*a* is fitted with a sound wave generator 58 and the opposite end face thereof with the second electric signal-generating device 46 in the same manner as in the first embodiment of FIG. 1. The sound wave generator 58 is operated by a pulse generator 60 to introduce a sound wave into the core member 20*a*. In this case, an output from the pulse generator 60 is directly used as the first electric signal S1. This first electric signal S1 is generally fully strong and is allowed to be conducted to the time interval-measuring devcie 48 without the necessity of being provided with an amplifier or filter. On the other hand, the second electric signal S2-*b* denoting a sound wave slowly propagating through the core 20 is attenuated during transmission and consequently is made to pass through the amplifier 52 and also through the filter 54 provided for the same reason as described in connection with the first embodiment of FIG. 1. Compensation for the time delay of said second signal conducted through the filter 54 is effected by operation of the switch 53 in the same manner as in FIG. 1, namely, by purposely causing the first electric signal S1 to pass through the filter 54 for measurement of the time delay sustained by said signal during transmission through the filter 54.

The sound wave generator 58 consists of any of various types such as a piezoelectric element and magnetostrictive element, and in one case may be formed of the aforesaid accelerometer. Where the pulse generator 60 impresses a pulse across the electrodes of said sound wave generator 58, then the generator 58 gives forth a sound wave, said sound wave being introduced into the core member 20a at one end face 56. The pulse generator 60 may consist of "Pulse Generator Model G 710" manufactured by E-H Research Laboratories, Inc. of the Unites States of America.

FIG. 5 is a block circuit diagram of still another embodiment of this invention where the time interval-measuring device consists of a digital counter 104. According to this embodiment, the first electric signal S1 is conducted from a terminal 100 through an amplifier 50 to a trigger circuit 102. A trigger pulse generated in said trigger circuit 102 is delivered to the digital counter 104. The second electric signal S2-b is transmitted from a terminal 106 to a trigger circuit 108 through an amplifier 52 and filter 54. A trigger pulse produced in said trigger circuit 108 is supplied to the digital counter 104, which in turn measures a time interval between both first and second electric signals S1, S2-b and digitally indicates a measured value of said time interval. In this case, the time delay of the second electric signal S2-b passing through the filter 54 is measured by changing over the operation of the switch 53 in the same manner as in FIG. 1 to correct the digitally indicated value of said time interval.

Figure 6:
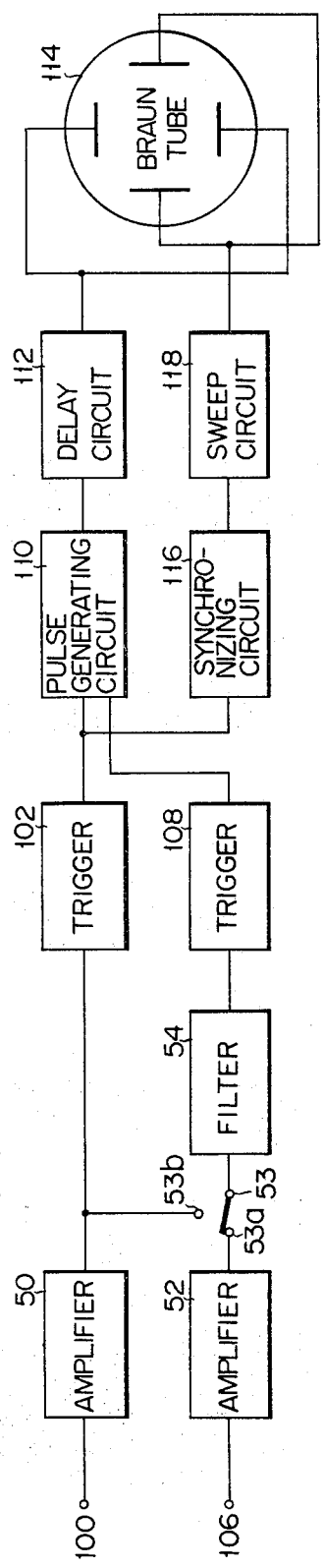
FIG. 6 is a block circuit diagram of a further embodiment of the invention where the time interval-measuring device consists of a Braun tube.
Figure 7:
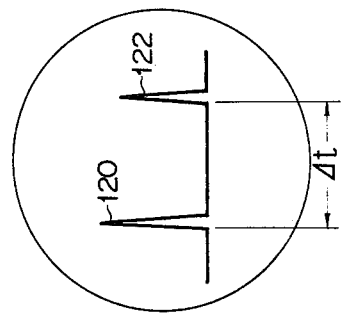
FIG. 7 shows a time interval between the first and second electric signals appearing on the Braun tube of FIG. 6.

FIG. 6 is a block circuit diagram of a further embodiment of this invention where the time interval-measuring device consists of a Braun tube 114. As in FIG. 5, the first electric signaal S1 is normally supplied from the terminal 100 to the pule generating circuit 110 through the amplifier 50 and trigger circuit 102, and the second electric signal S2-b is always conducted from the terminal 106 to said pulse generating circuit 110 through the amplifier 52 and filter 54. The first electric signal S1 is delivered to both pulse generating circuit 110 and synchronizing circuit 116 immediately to operate a sweep circuit 118, thereby causing a spot on the Braun tube to be swept in a horizontal direction. The pulses which the pulse generating circuit 110 gives forth upon receipt of the first and second electric signals S1, S2-b are conducted through a delay circuit 112 to the Braun tube 114 to cause a spot thereon to be shifted in a vertical direction. A spot shifted horizontally as well as vertically on the Braun tube 114 presents a pattern shown in FIG. 7. A time interval $\Delta t$ between the first and second electric signals S1, S2-b is measured from a time interval between two pulses 120, 122 indicated in FIG. 7. However, this measured time interval is further corrested by the extent of a time delay sustained by the second electric signal S2-b. This time delay is obtained by the changed operation of the switch 53 in the same manner as in FIG. 1.

Figure 8:
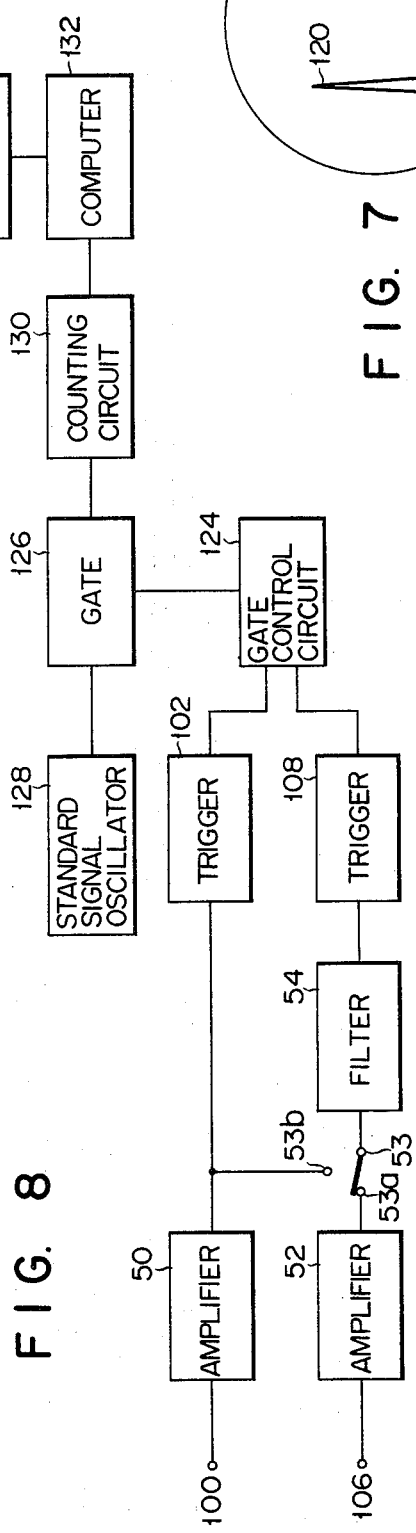
FIG. 8 is a block circuit diagram of an arrangement of a counting circuit, computer and printer for measuring a time interval between the first and second electric signals, calculating the velocity of a sound wave propagating through the body of a laminated iron core, and drawing out a measured value of the magnitude of clamping load stored in a memory device and recording it on a printer.

FIG. 8 is a block circuit diagram of an arrangement including a counting circuit 130, computer 132 and printer 134 to measure a time interval between the first and second electric signals S1, S2-b, calculate the velocity of a sound slowly propagating the core 20 (not shown) from the corrected time interval, thereby determining the magnitude of clamping load applied to the core 20 (not shown), and finally record the velocity of the sound and clamping load. The first electric signal S1 is normally conducted from the terminal 100 through the trigger circuit 102 to a gate control circuit 124, and the second electric signal S2-b is always supplied to said gate control circuit 124 from the terminal 106 through the switch 53, filter 54 and the trigger circuit 108. The gate control circuit 124 opens a gate circuit 126 upon receipt of the first electric signal S1 and closes said gate circuit 126 upon receipt of the second electric signal S2-b. While the gate circuit 126 is left open, a signal generated by a standard signal oscillator 128 is supplied to a counting circuit 130 which measures a time interval between the first and second electric signals S1, S2-b. The measured value of the time interval is transmitted to a computer 132, which in turn calculates the propagating velocity of a sound wave by a calculating formula for correcting said time interval by an extent of time delay sustained by the second electric signal S2-b conducted through the filter 54, and by a calculating formula determining the propagating velocity of a sound wave from the corrected time interval with reference to previously provided data on a relationship between the magnitude of clamping load and the corresponding propagating velocity of a sound wave, said calculation formula and previously provided data being already stored in a memory device, and finally determines the magnitude of clamping load applied to a laminated iron core 20 (not shown). The magnitude of the clamping load and, when required, the propagating velocity of a sound wave are generally displayed on an indication type counter and, if desired, recorded by connecting a printer 134 to a computer 132. The switch 53 is operated in the same manner as in the first embodiment of FIG. 1 when measurement is to be made of a time delay sustained by the second electric signal S2-b during transmission through the filter 54.

What we claim is:

1. A method for measuring the magnitude of a clamping load applied to a laminated iron core of an electric machine which comprises the steps of introducing a sound wave into the core at one end face thereof and immediately generating a first electric signal; producing a second electric signal when the sound wave propagates through the core and reaches the opposite end face therof; measuring a time interval between the first and second electric signals; dividing a distance between both end faces of the core by the measured time interval to calculate the velocity of a sound wave propagating through the core; and determining the magntiude of clamping load applied to the core from the calculated propagating velocity of a sound wave with reference to previously provided data on a relationship between the magnitude of said clamping force and the corresponding propagating velocity of a sound wave.

2. An apparatus for measuring the magnitude of a clamping load applied to a laminated iron core of an electric machine which comprises a device for introducing a sound wave into the core at one end face thereof; a device to generate a first electric signal upon introduction of the sound wave into the core; a device fitted to the opposite end face of the core to give forth a second electric signal when the sound wave passing through the core reaches said opposite end face; and a device for measuring a time interval between the first and second electric signals, whereby the magnitude of clamping load applied to the core is determined by calculating the propagating velocity of the sound wave using a time interval measured by said time interval-measuring device with reference to previously prepared data on a relationship between the magnitude of clamping pressure applied to the core and the corresponding velocity of the sound wave propagating through the core.

3. An apparatus according to claim 2, wherein the device for introducing a sound wave into the laminated iron core at one end face thereof is a wooden mallet, and the device for giving forth the first electric signal is a first electric signal generator fitted to one end face of the laminated iron core.

4. An apparatus according to claim 2, wherein the device for introducing a sound wave into the laminated iron core at one end face thereof consists of a pulse generator fitted to said one end face of the core and a sound wave generator actuated by an output from the pulse generator; and said pulse generator concurrently acts as the first electric signal generator to produce an output as the first electric signal.

5. An apparatus according to claim 2, which further comprises a filter provided in a circuit for conducting the second electric signal to the time interval-measuring device and designed to allow the passage of only the second electric signal propagating through the laminated iron core.

6. An apparatus according to claim 2, wherein the time interval-measuring device cmprises an electromagnetic oscillograph for measuring a time interval between the first and second electric signals from a distance between the oscillograms of said two electric signals presented on a chart.

7. An apparatus according to claim 2, wherein the time interval-measuring device comprises a Braun tube capable of measuring a time interval between the first and second electric signals from a distance between the wave forms of said first and second electric signals displayed on the fluorescent surface of said Braun tube.

8. An apparatus according to claim 2, wherein the time interval-measuring device comprises a digital counter for digitally indicating a time interval between the first and second electric signals.

9. An apparatus according to claim 2, which further comprises a computer connected to the time interval-measuring device to calculate the propagating velocity of a sound wave and the magnitude of clamping pressure applied to the laminated iron core from said propagating velocity.

10. An apparatus according to claim 2, which further comprises a switch capable of being so operated as to attain the measurement of time delay sustained by the electric signal conducted through a filter provided in a circuit for delivering the electric signals to the time interval-measuring device, thereby correcting the previously measured time interval between the first and second electric signals by the extent of said measured time delay.

* * * * *